United States Patent
Seyler et al.

(12)

(10) Patent No.: US 6,872,401 B2
(45) Date of Patent: *Mar. 29, 2005

(54) COSMETIC/DERMATOLOGICAL COMPOSITIONS COMPRISING A TETRAHYDROCURCUMINOID AND AN AMIDE OIL

(75) Inventors: Nathalie Seyler, Maisons-Alfort (FR); Cécile Fiandino, Paris (FR); Didier Candau, Bievres (FR)

(73) Assignee: L'Oreal, Paris (FR)

( * ) Notice: Subject to any disclaimer, the term of this patent is extended or adjusted under 35 U.S.C. 154(b) by 33 days.

This patent is subject to a terminal disclaimer.

(21) Appl. No.: 10/400,388

(22) Filed: Mar. 28, 2003

(65) Prior Publication Data

US 2004/0009200 A1 Jan. 15, 2004

Related U.S. Application Data

(60) Provisional application No. 60/377,960, filed on May 7, 2002.

(30) Foreign Application Priority Data

Mar. 28, 2002 (FR) ............................. 02 03932

(51) Int. Cl.$^7$ ............................. A61K 7/00; A61K 7/42; A61K 7/44
(52) U.S. Cl. ............................. 424/401; 424/59; 424/60; 424/400
(58) Field of Search ............................. 424/59, 60, 400, 424/401

(56) References Cited

FOREIGN PATENT DOCUMENTS

| DE | 101 21 069 A | 10/2002 |
|----|--------------|---------|
| EP | 0 815 834 A | 1/1998 |
| EP | 0 928 608 A | 7/1999 |
| EP | 1 044 676 A | 10/2000 |
| EP | 1 108 419 A | 6/2001 |

OTHER PUBLICATIONS

Search Report issued in French Priority Counterpart FR 02/03932, issued on Dec. 5, 2002, 2 pages.

*Primary Examiner*—Shelley A. Dodson
(74) *Attorney, Agent, or Firm*—Burns, Doane, Swecker & Mathis, L.L.P.

(57) ABSTRACT

The invention relates to a cosmetic or dermatological composition containing a carrier comprising at least one fatty phase characterized in that it contains at least one derivative or a mixture of derivatives of 1,7-diphenyl-3,5-heptanedione having a particular structure and at least one oil having, in its structure, at least one amide unit.

The invention also relates to its uses in cosmetics and dermatology, in particular for preventing or combating the harmful effects of UV radiation and pollution on human keratinous materials, and more particularly for preventing and/or treating photoaging of the skin.

The invention also relates to a method for solubilizing a derivative or a mixture of derivatives of 1,7-diphenyl-3,5-heptanedione having a particular structure with at least one oil having, in its structure, at least one amide unit.

45 Claims, No Drawings

COSMETIC/DERMATOLOGICAL COMPOSITIONS COMPRISING A TETRAHYDROCURCUMINOID AND AN AMIDE OIL

CROSS-REFERENCE TO PRIORITY/PROVISIONAL APPLICATIONS

This application claims priority under 35 U.S.C. § 119 of FR-02/03932, filed Mar. 28, 2002, and of provisional application Ser. No. 60/377,960, filed May 7, 2002, both hereby expressly incorporated by reference.

BACKGROUND OF THE INVENTION

1. Technical Field of the Invention

The invention relates to a cosmetic or dermatological composition containing a carrier comprising at least one fatty phase characterized in that it contains at least one derivative or a mixture of derivatives of 1,7-diphenyl-3,5-heptanedione having a particular structure and at least one oil having, in its structure, at least one amide unit, and its cosmetic and dermatological uses, in particular against the harmful effects of UV radiation and pollution on human keratinous materials, and more particularly for the prevention and/or treatment of photoaging of the skin.

The invention also relates to a method for solubilizing a derivative or a mixture of derivatives of 1,7-diphenyl-3,5-heptanedione having a particular structure with at least one oil having, in its structure, at least one amide unit.

2. Description of the Prior Art

In the course of time, various signs appear on the skin which are very characteristic of aging, resulting in particular in a modification of the structure and the functions of the skin.

This aging, which is of a physiological nature, may be accelerated by environmental factors such as repeated exposure of the skin to sunlight, and in particular to ultraviolet A radiation, to pollution in particular, or to diesel particles or to cigarette smoke. The environmental action on the constituents of the skin (fibers, cells, enzymes) and on the sebum secreted by the skin causes, in particular, the formation of oxygenated free radicals. Now, these radicals cause substantial oxidative damage, in particular in the cell membranes (permeability of the membranes), the cell nuclei (destruction of DNA), and the tissues, in particular the connective tissue (degradation of the elastin and collagen fibers). This damage leads in particular to a loss of firmness and elasticity of the skin.

It has, in addition, been suggested that the free radicals could be involved in the process of production of melanin leading to the pigmentation of the skin.

The mechanism of formation of melanin is particularly complex and schematically involves the following main steps:

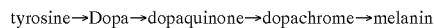

tyrosine→Dopa→dopaquinone→dopachrome→melanin

Tyrosinase (monophenol dihydroxyphenylalanine: oxygen oxidoreductase EC 1.14.18.1) is the key enzyme involved in this succession of reactions. It catalyses in particular the reaction of conversion of tyrosine to Dopa (dihydroxyphenylalanine) by virtue of its hydroxylase activity. Now, some authors think that the step of hydroxylation of tyrosine to Dopa could be initiated by OH° radicals (C. Montastier et al., Méthodes d'objectivation des effets des agents dépigmentants chorl'homme [Methods of objectifying the effects of depigmenting agents in humans], J. Med. Esth. and Chir. Derm., Vol. XXII, 86, June 1995, pp. 93–103).

The free radicals formed under the effect of environmental factors could therefore cause an increase in the formation of melanin, and thus cause or intensify certain undesirable hyperpigmentation such as idiopathic melasma, which occur during pregnancy ("mask of pregnancy" or chloasma) or during oestro-progestational contraception, or localized hyperpigmentation such as the senile pigmented spots termed actinic lentigines.

It is therefore necessary to protect the skin against these free radicals.

This protective function is usually provided by enzymes present in the cutaneous tissue. However, under certain circumstances, the role of these enzymes is not sufficient to completely block the destructive action of free radicals.

The tetrahydrocurcuminoids obtained by the reduction of curcumin or which are synthesized as described in the articles "Synthesis and antibacterial activity of tetrahydrocurcuminoids; S Venkateswarlu, M Rambabu, G V Subbaraju and S Satyanarayana; Asian Journal of Chemistry-2000-1-141–144", "Synthesis of naturally occurring curcuminoids and related compounds; U Pedersen, P B Rasmussen, S O Lawesson; Liebigs Ann. Chem.-1985-1557–1569, patent applications JP 02051595, JP 02069431, JP 02049747 and JP 02128133, patent U.S. Pat. No. 5,266,344 and application WO 00/61162 have already been used in cosmetics as agent for protecting skin against the effects of UV radiation (JP 06128133), as antioxidant and/or as anti-free radical agents in patent application WO 97/03674. They are also used in application WO 99/55352 in lightening or depigmenting compositions for the skin in combination with a depigmenting agent.

There are also known from patent application EP 1108419 cosmetic compositions for topical application to the skin, containing at least one tetrahydrocurcuminoid such as tetrahydrocurcumin and/or tetrahydrodemethoxycurcumin and/or tetrahydrobisdemethoxycurcumin or mixtures thereof. They are used for protecting human keratinous materials against the harmful effects due to various environmental factors: UV radiation, smoke, ozone, polluting substances. They are also recommended for combating the formation of free radicals and intrinsic or extrinsic skin aging. It is also known, in application WO 99/22728, that tetrahydrocurcuminoids are also active as 5α-reductase inhibitors.

During its research studies, the applicant observed that certain derivatives of 1,7-diphenyl-3,5-heptanedione, including tetrahydrocurcuminoids, which are active as antioxidants and/or as anti-free radical agents, substantially lost their efficacy in common cosmetic carriers comprising at least one fatty phase (in particular emulsions) because of their very low solubility in most oils commonly used and led to microscopically unstable formulations over time because they crystallize and form a deposit in the carrier. This instability of the tetrahydrocurcuminoids can, in addition, modify the appearance of the compositions containing them.

Among the oils commonly used in cosmetics, there may be mentioned mineral oils such as those of the paraffin type (MARCOL 82 from Esso) or hydrocarbons such as isohexadecane (PERMTHYL 101A from BAYER); oils of plant origin such as refined apricot stone oil (MP301 from Nestle); liquid waxes such as liquid jojoba wax (Pure Golden Jojoba Oil from DESERT WHALE); fatty acid esters such as dicaprylyl maleate (BERNEL ESTER from DOM), dicaprylyl carbonate (CETIOL CC from Cognis), tridecyl trimellitate (DUB TMTD from Stearine Dubois), dioctyl maleate (CERAPHYL CM5 from Rhodia Chimie), isopropyl palmitate, isononyl isononanoate (WICKENOL 151 from Alzo) and $C_{12}$–$C_{15}$ alcohol benzoates (FINSOLV TN from WITCO); $C_6$–$C_{18}$ fatty acid triglycerides such as caprylic/capric acid triglyceride (MYRITOL 318 from Cognis).

SUMMARY OF THE INVENTION

The applicant has now discovered, unexpectedly and surprisingly, that oils having in their structure at least one amide functional group made it possible to solubilize, in large quantities, 1,7-diphenyl-3,5-heptanedione derivatives of formula (I), defined below, such as tetrahydrocurcuminoids in cosmetic carriers comprising a fatty phase such as emulsions and to obtain formulations which are stable over time and which have an improved efficacy towards human keratinous materials against the harmful effects of UV radiation and/or of pollution, in particular against photoaging of the skin.

The expression human keratinous materials is understood to mean the skin, the lips, the scalp, the hair, the eyelashes, the eyebrows, and the nails.

This discovery forms the basis of the present invention.

A first subject of the invention relates to a cosmetic or dermatological composition containing a carrier comprising at least one fatty phase, characterized in that it contains at least one derivative or a mixture of derivatives of 1,7-diphenyl-3,5-heptanedione of formula (I), defined below, and at least one oil having, in its structure, at least one amide unit.

Another subject of the invention relates to the cosmetic use of a composition according to the invention for preventing or combating the harmful effects of UV radiation and/or of pollution on human keratinous material, and more particularly the skin.

The expression "pollution" is understood to mean both "external" pollution, due for example to diesel particles, to ozone and to heavy metals, and "internal" pollution which may be due in particular to emissions of solvents from paint, carpet adhesive, insulating materials or wallpaper (such as toluene, styrene, xylene or benzaldehyde), or cigarette smoke. All these pollutants are indeed capable of generating free radicals directly or indirectly.

Another subject of the invention relates to the use of a composition for the preparation of a product for preventing the formation of free radicals in contact with the skin and/or for neutralizing the free radicals already formed.

Another subject of the invention relates to the use of a composition according to the invention for the preparation of a product for treating skin damaged by the harmful effects of UV radiation and of pollution and in particular for treating skin dried, cracked, irritated or burnt by the sun and/or pollution.

Another subject of the invention relates to the use of a composition according to the invention for the preparation of a product intended for preventing and/or treating the signs of skin aging, and in particular for preventing and/or treating loss of firmness and/or elasticity of the skin.

The subject of the invention is also the cosmetic use of this composition for preventing or reducing the formation of pigmented spots and/or for lightening or depigmenting the skin.

Another subject of the invention relates to the use of at least one oil having, in its structure, at least one amide unit in a cosmetic or dermatological composition containing at least one derivative or a mixture of 1,7-diphenyl-3,5-heptanedione of formula (I) for solubilizing the said derivative or a mixture of derivatives of formula (I).

The invention also relates to a method for solubilizing at least one derivative or a mixture of derivatives of 1,7-diphenyl-3,5-heptanedione of formula (I) in a cosmetic or dermatological composition containing at least one fatty phase, consisting in using at least one oil having, in its structure, at least one amide unit in a sufficient quantity which makes it possible to solubilize, on its own, all the 1,7-diphenyl-3,5-heptanedione derivative(s).

Other subjects of the invention will emerge later in the description.

DETAILED DESCRIPTION OF BEST MODE AND SPECIFIC/PREFERRED EMBODIMENTS OF THE INVENTION

The expression "oil having, in its structure, at least one amide unit" is understood to mean, in the whole text of the description, any compound containing, in its chemical structure, at least one amide group (or functional group) of the type:

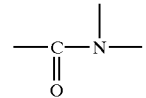

and simultaneously having the following characteristics:
(a) liquid at 25° C.,
(b) insoluble or immiscible with water at 25° C.
(c) does not exhibit emulsifying properties.

The 1,7-diphenyl-3,5-heptanedione derivatives in accordace with the invention correspond to the following formula (I):

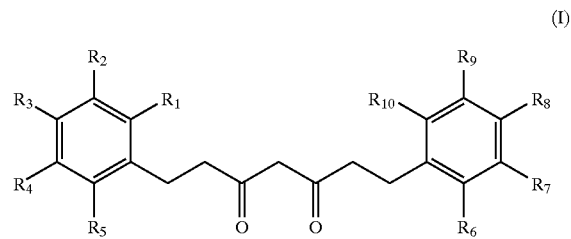

in which:
$R_1$, $R_2$, $R_3$, $R_4$, $R_5$, $R_6$, $R_7$, $R_8$, $R_9$ and $R_{10}$, which are identical or different, are chosen from:
(i) a hydrogen atom;
(ii) a linear or branched $C_1$–$C_4$ alkyl radical;
(iii) a radical $OR_{11}$ in which $R_{11}$ is chosen from a hydrogen atom, a linear or branched $C_1$–$C_4$ alkyl radical, a radical $PO(OX_1)(OX_2)$ or a radical $SO_2(OX_3)$ in which $X_1$, $X_2$ and $X_3$, which are identical or different, denote a hydrogen atom or an alkali metal cation or $NH_4^+$; it being possible for $X_1$ and $X_2$ to also denote together a divalent metal cation,
(iv) an acyl radical $R_{12}CO$ in which $R_{12}$ is chosen from $C_1$–$C_{30}$ hydrocarbon radicals, which are linear or branched, saturated or unsaturated, hydroxylated or nonhydroxylated, carboxylated or noncarboxylated;
(v) a glycosyl or uronyl radical; when a radical $R_1$ to $R_{10}$ denotes a residue $OR_{11}$, it can also form with the aromatic ring to which it is attached and an adjacent radical a ring containing 5 or 6 atoms;

it being understood that at least one of the radicals $R_1$ to $R_{10}$ denotes a residue $OR_{11}$.

In formula (I) described above, the alkyl radicals may denote in particular the methyl, ethyl, propyl, isopropyl, n-propyl, butyl, n-butyl or tert-butyl radicals; preferably, the alkyl radical denotes the methyl radical.

In formula (I) described above, the glycosyl radical denotes more particularly a glucosyl radical.

In formula (I) described above, the uronyl radical denotes more particularly a mannuronyl or glucuronyl radical.

The compounds of formula (I) are known per se. The tetrahydrocurcuminoids in accordance with the invention are obtained by reducing curcumin or are synthesized as described in the articles "Synthesis and antibacterial activity of tetrahydrocurcuminoids; S Venkateswarlu, M Rambabu, G V Subbaraju and S Satyanarayana; Asian Journal of Chemistry-2000-1–141–144", "Synthesis of naturally occurring curcuminoids and related compounds; U Pedersen, P B Rasmussen, S O Lawesson; Liebigs Ann. Chem.-1985-1557–1569, patent applications JP 02051595, JP 02069431, JP 02049747 and JP 02128133, patent U.S. Pat. No. 5,266,344 and application WO 00/61162.

Among the preferred compounds of formula (I) according to the present invention, there may be mentioned:

1,7-bis(3-hydroxy-4-methoxyphenyl)-3,5-heptanedione or tetrahydrocurcumin (THC) of structure:

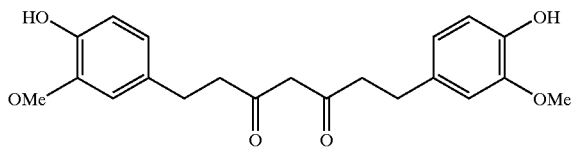

1-(3-methoxy-4-hydroxyphenyl)-7-(4'-hydroxyphenyl)-3,5-heptanedione or tetrahydrodemethoxycurcumin (THDC) of structure:

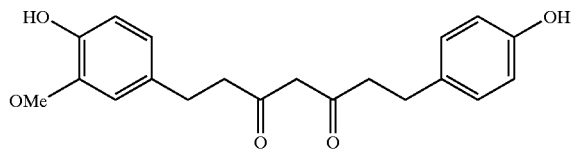

1,7-bis(4-hydroxyphenyl)-3,5-heptanedione or tetrahydrobisdemethoxycurcumin (THBDC) of structure:

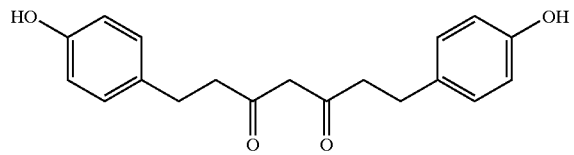

1,7-bis(3,4-dihydroxyphenyl)-3,5-heptanedione of structure:

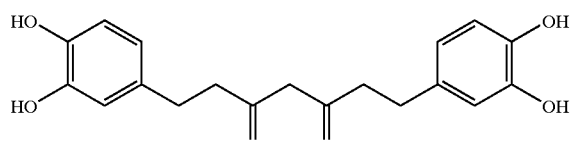

and mixtures thereof.

A particular form of the invention consists in using, as sole compound of formula (I), 1,7-bis(3-hydroxy-4-methoxyphenyl)-3,5-heptanedione or tetrahydrocurcumin (THC).

Another particular form of the invention consists in using a mixture of compounds of formula (I) consisting:
of tetrahydrocurcumin;
of tetrahydrodemethoxycurcumin; and
of tetrahydrobisdemethoxycurcumin.

There will be used still more particularly a mixture consisting:
of 70 to 95% by weight of tetrahydrocurcumin;
of 4 to 25% by weight of tetrahydrodemethoxycurcumin; and
of 0.5 to 10% by weight of tetrahydrobisdemethoxycurcumin;
and still more particularly a mixture consisting:
of 75 to 90% by weight of tetrahydrocurcumin;
of 8 to 20% by weight of tetrahydrodemethoxycurcumin; and
of 1 to 5% by weight of tetrahydrodemethoxycurcumin like the product described and synthesized in application WO 00/61162 and provided by the company SABINSA CORPORATION under the trademark Tetrahydrocurcuminoids CG or Tetrahydrocurcuminoids.

In general, the compound(s) of formula (I) present in the composition are completely dissolved in the carrier of the composition.

The compounds of formula (I) according to the invention preferably represent from 0.001% to 10% by weight approximately of the total weight of the cosmetic composition, more particularly from 0.01% to 5%, and still more preferably from 0.1% to 5% by weight approximately of this weight.

The oil or oils having, in their structure, at least one amide unit in accordance with the invention are preferably chosen from the compounds of the following formula (II):

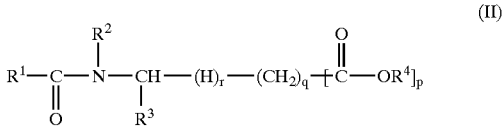

in which:
the radical $R^1$ represents an optionally functionalized, aliphatic, cycloaliphatic or cyclic, saturated or unsaturated, monovalent hydrocarbon radical containing from 1 to 30 carbon atoms, preferably from 1 to 22 carbon atoms, inclusive;

the radicals $R^2$, $R^3$ and $R^4$, which may be identical or different, represent hydrogen or optionally functionalized, aliphatic, cycloaliphatic or cyclic, saturated or unsaturated, monovalent hydrocarbon radicals containing from 1 to 30 carbon atoms, preferably from 1 to 22 carbon atoms, inclusive;

r is 0 or 1;

q is an integer from 0 to 2;

p equals 0 or 1, provided that when p=1 then r=0 and when p=0, then q=0 and r=0.

As examples of aliphatic saturated hydrocarbon radicals, there may be mentioned in particular substituted or unsubstituted, linear or branched $C_1$–$C_{30}$, preferably $C_1$–$C_{22}$, alkyl radicals, and in particular methyl, ethyl, n-propyl, isopropyl, n-butyl, isobutyl, tert-butyl, pentyl, n-amyl, isoamyl, neopentyl, n-hexyl, n-heptyl, n-octyl, 2-ethylhexyl, tert-octyl, decyl, lauryl and octadecyl radicals.

By way of examples of cyclic saturated hydrocarbon radicals, there may be mentioned in particular cyclopentyl and cyclohexyl radicals, optionally substituted, in particular with alkyl radicals.

As examples of aliphatic unsaturated hydrocarbon radicals, there may be mentioned in particular substituted or unsubstituted, linear or branched $C_2$–$C_{30}$, preferably $C_2$–$C_{22}$, alkenyl or alkynyl radicals, in particular vinyl, allyl, oleyl and linoleyl radicals.

As examples of cyclic unsaturated hydrocarbon radicals, there may be mentioned in particular aryl radicals such as phenyl and naphthyl, optionally substituted, in particular with alkyls, such as for example the tolyl radical, and as examples of unsaturated cycloaliphatic radicals, there may be mentioned more particularly benzyl and phenylethyl radicals.

The expression functionalized radicals is understood to mean more particularly radicals containing, in their chemical structure, both in the principle chain and on a side chain, one or more functional groups in particular of the ester, ether, alcohol, amine, amide and ketone type, but preferably of the ester type.

The preferred amide oils of formula (II) are chosen from those where:
$R^1$ represents a linear or branched $C_1$–$C_{22}$ alkyl radical; a linear or branched $C_2$–$C_{22}$ alkenyl radical; an aryl radical;
$R^2$ represents a hydrogen atom or a linear or branched $C_1$–$C_6$ alkyl group;
$R^3$ represents a hydrogen atom or a linear or branched $C_1$–$C_6$ alkyl group;
$R^4$ represents a linear or branched $C_1$–$C_{10}$ alkyl radical, or a linear or branched $C_2$–$C_{10}$ alkenyl radical or a sterol residue.

In formula (II) presented above, the group $R^1$ (CO)— is an acyl group of an acid preferably chosen from the group formed by acetic acid, toluic acid, capric acid, lauric acid, myristic acid, palmitic acid, stearic acid, behenic acid, linoleic acid, linolenic acid, oleic acid, isostearic acid, 2-ethylhexanoic acid, coconut oil fatty acids, palm kernel oil fatty acids. These acids may, in addition, have a hydroxyl group.

In formula (II), when p equals 1, the portion —N($R^2$)CH($R^3$) ($CH_2$)q(CO)— of the amino acid ester is preferably chosen from those corresponding to the following amino acids: glycine, alanine, valine, leucine, isoleucine, serine, threonine, proline, hydroxyproline, β-alanine, N-butyl-β-alanine, aminobutyric acid, aminocaproic acid, sarcosine or N-methyl-β-alanine.

In formula (II), when p equals 1, the part of the amino acid esters corresponding to the group $OR^4$ may be obtained from alcohols chosen from the group formed by methanol, ethanol, propanol, isopropanol, butanol, tert-butanol, isobutanol, 3-methyl-1-butanol, 2-methyl-1-butanol, pentanol, hexanol, cyclohexanol, octanol, 2-ethylhexanol, decanol, lauryl alcohol, myristyl alcohol, cetyl alcohol, ketostearyl alcohol, stearyl alcohol, oleyl alcohol, behenyl alcohol, jojoba alcohol, 2-hexadecyl alcohol, 2-octyldodecanol alcohol and isostearyl alcohol.

The oils having, in their structure, at least one amide functional group of formula (II) in accordance with the invention are known per se. Some are in particular described with their modes of preparation in patent applications EP-1,044,676 and EP-0,928,608 from the company AJINOMOTO CO. Others are known in cosmetics as insect repellents such as N-acetyl-N-butylaminopropionate or N,N-diethyltoluamide.

Among the compounds of formula (II) which are particularly preferred, there may be mentioned:
(1) N-acetyl-N-butylaminopropionate of the following formula:

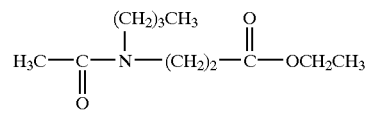

such as the product sold under the trademark Repellent R3535 by the company MERCK;
(2) isopropyl N-lauroylsarcosinate of formula:

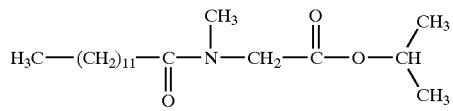

such as the product sold under the name ELDEW SL-205 by the company Ajimoto;
(3) N,N-diethyltoluamide of formula:

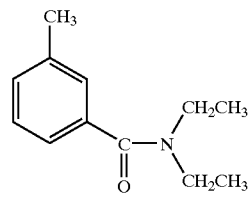

such as the product sold under the trademark DEET by the company Showa Denko.

The oil or oils having, in their structure, at least one amide functional group as defined above are present in the compositions according to the invention in concentrations preferably ranging from 0.1% to 40% by weight and more preferably from 1% to 20% by weight relative to the total weight of the composition. The oil or oils having, in their structure, at least one amide functional group will be preferably used in a sufficient quantity which makes it possible to solubilize, on (its) their own, the total quantity of derivative(s) of formula (I) in the composition.

The compositions according to the invention are suitable for topical application to human keratinous materials, in particular the skin. They may be provided in all galenic forms containing at least one fatty phase which are normally used for this type of application, in particular in the form of an oily solution, an oil-in-water or water-in-oil or multiple emulsion, a silicone emulsion, a microemulsion or nanoemulsion, an oily gel or an anhydrous liquid, pasty or solid product.

The compositions according to the invention may be used for preventing or combating the harmful effects of UV radiation and of pollution on human keratinous materials, and more particularly the skin.

The expression "pollution" is understood to mean both "external" pollution, due for example to diesel particles, to ozone and to heavy metals, and "internal" pollution which may be due in particular to emissions of solvents from paint, carpet adhesive, insulating materials or wallpaper (such as toluene, styrene, xylene or benzaldehyde), or cigarette smoke. All these pollutants are indeed capable of generating free radicals directly or indirectly.

Preferably, these compositions according to the invention further contain at least one agent which screens out UV radiation.

The agents which screen out ultraviolet radiation may be chosen from organic UV screening agents, inorganic UV radiation screening agents, or mixtures thereof.

The organic UV screening agents in accordance with the invention may be water-soluble, fat-soluble or insoluble in the customary cosmetic solvents. They are chosen in particular from anthranilates; cinnamic derivatives; dibenzoylmethane derivatives; salicylic derivatives; camphor derivatives; triazine derivatives such as those described in patent applications U.S. Pat. No. 4,367,390, EP-863,145, EP-517,104, EP-570,838, EP-796,851, EP-775,698, EP-878,469 and EP-933,376; benzophenone derivatives, in particular those described in applications EP-A-1,046,391 and DE-1-0,012,408; β,β'-diphenylacrylate derivatives, benzotriazole derivatives, benzimidazole derivatives; imidazolines; bisbenzoazolyl derivatives as described in patents EP-669,323 and U.S. Pat. No. 2,463,264; p-aminobenzoic acid (PABA) derivatives; methylene bis(hydroxyphenylbenzotriazole) derivatives as described in applications U.S. Pat. Nos. 5,237,071, 5,166,355, GB-2,303,549, DE-1-9,726,184 and EP-893,119; screening polymers and screening silicones such as those described in particular in application WO 93/04665; dimers derived from a-alkylstyrene such as those described in patent application DE-1-9,855,649; 4,4-diarylbutadiene derivatives such as those described in patent applications EP-0-967,200, DE-1-9,755,649 and EP-1-133,981; amino-substituted hydroxybenzophenones such as the structures described in EP-1-046,391 and EP-1-133,980; and mixtures thereof.

As examples of organic screening agents, there may be mentioned those designated under their INCI name:

Para-aminobenzoic Acid Derivatives:
PABA,
Ethyl PABA,
Ethyl Dihydroxypropyl PABA,
Ethylhexyl Dimethyl PABA sold in particular under the name "ESCALOL 507" by ISP,
Glyceryl PABA,
PEG-25 PABA sold under the name "UVINUL P25" by BASF,
Salicylic Derivatives:
Homosalate sold under the name "Eusolex HMS" by Rona/EM Industries,
Ethylhexyl Salicylate sold under the name "NEO HELIOPAN OS" by Haarmann and REIMER,
Dipropyleneglycol Salicylate sold under the name "DIPSAL" by SCHER,
TEA salicylate sold under the name "NEO HELIOPAN TS" by Haarmann and REIMER,
Dibenzoylmethane derivatives:
Butyl Methoxydibenzoylmethane sold in particular under the trademark "PARSOL 1789" by HOFFMANN LA ROCHE, Isopropyl Dibenzoylmethane,
Cinnamic Derivatives:
Ethylhexyl Methoxycinnamate sold in particular under the trademark "PARSOL MCX" by HOFFMANN LA ROCHE,
Isopropyl Methoxycinnamate,
Isoamyl Methoxycinnamate sold under the trademark "NEO HELIOPAN E 1000" by HAARMANN and REIMER,
Cinoxate,
DEA Methoxycinnamate,
Diisopropyl Methylcinnamate,
Glyceryl Ethylhexanoate Dimethoxycinnamate,
β,β'-Diphenylacrylate Derivatives:
Octocrylene sold in particular under the trademark "UVINUL N539" by BASF,
Etocrylene sold in particular under the trademark "UVINUL N35" by BASF, Benzophenone Derivatives:
Benzophenone-1 sold under the trademark "UVINUL 400" by BASF,
Benzophenone-2 sold under the trademark "UVINUL D50" by BASF,
Benzophenone-3 or Oxybenzone sold under the trademark "UVINUL M40" by BASF,
Benzophenone-4 sold under the trademark "UVINUL MS40" by BASF,
Benzophenone-5,
Benzophenone-6 sold under the trademark "Helisorb 11" by Norquay,
Benzophenone-8 sold under the trademark "Spectra-Sorb UV-24" by American Cyanamid,
Benzophenone-9 sold under the trademark "UVINUL DS-49" by BASF,
Benzophenone-12,
n-hexyl 2-(4-diethylamino-2-hydroxybenzoyl)benzoate,
Benzylidenecamphor Derivatives:
3-Benzylidenecamphor manufactured under the name "MEXORYL SD" by CHIMEX,
4-Methylbenzylidenecamphor sold under the name "EUSOLEX 6300" by Merck,
Benzylidene Camphor Sulphonic Acid manufactured under the name "MEXORYL SL" by CHIMEX,
Camphor Benzalkonium Methosulphate manufactured under the name "MEXORYL SO" by CHIMEX,
Terephthalylidene Dicamphor Sulphonic Acid manufactured under the name "MEXORYL SX" by CHIMEX,
Polyacrylamidomethyl Benzylidene Camphor manufactured under the name "MEXORYL SW" by CHIMEX,
Phenylbenzimidazole Derivatives:
Phenylbenzimidazole Sulphonic Acid sold in particular under the trademark "EUSOLEX 232" by MERCK,
Disodium Phenyl Dibenzimidazole Tetrasulphonate, sold under the trademark "NEO HELIOPAN AP" by Haarmann and REIMER,
Triazine Derivatives:
Anisotriazine sold under the trademark "TINOSORB S" by CIBA GEIGY
Ethylhexyltriazone sold in particular under the trademark "UVINUL T150" by BASF,
Diethylhexyl Butamido Triazone sold under the trademark "UVASORB HEB" by SIGMA 3V,
Phenylbenzotriazole Derivatives:
Drometrizole Trisiloxane sold under the name "Silatrizole" by RHODIA CHIMIE,
Methylene bis-Benzotriazolyl Tetramethylbutylphenol, sold in solid form under the trademark "MIXXIM BB/100" by FAIRMOUNT CHEMICAL or in micronized form as an aqueous dispersion under the trademark "TINOSORB M" by CIBA SPECIALTY CHEMICALS,
Anthranilic Derivatives:
Menthyl anthranilate sold under the trademark "NEO HELIOPAN MA" by Haarmann and REIMER,
Imidazoline derivatives:
Ethylhexyl Dimethoxybenzylidene Dioxoimidazoline Propionate,
Benzalmalonate Derivatives:
Polyorganosiloxane with benzalmalonate functional groups, as Polysilicone-15 sold under the trademark "PARSOL SLX" by HOFFMANN LA ROCHE
4,4-diarylbutadienes:
1,1-dicarboxy-(2,2'-dimethyl)-4,4-diphenylbutadiene and mixtures thereof.

The most particularly preferred organic UV-screening agents are chosen from the following compounds:

Ethylhexyl Salicylate,
Butyl Methoxydibenzoylmethane,
Ethylhexyl Methoxycinnamate,
Octocrylene,
Phenylbenzimidazole Sulfonic Acid,
Terephthalylidene Dicamphor Sulfonic Acid,
Benzophenone-3,
Benzophenone-4,
Benzophenone-5,
n-hexyl 2-(4-diethylamino-2-hydroxybenzoyl)benzoate,
4-Methylbenzylidenecamphor,
Disodium Phenyl Dibenzimidazole Tetrasulfonate,
Anisotriazine,
Ethylhexyl triazone,
Diethylhexyl Butamido Triazone,
Methylene bis-Benzotriazolyl Tetramethylbutylphenol,
Drometrizole Trisiloxane,
Polysilicone-15,
1,1-dicarboxy-(2,2'-dimethyl)-4,4-diphenylbutadiene and mixtures thereof.

The inorganic screening agents are generally pigments or nanopigments (mean size of the primary particles: generally between 5 nm and 100 nm, preferably between 10 nm and 50 nm) of metal oxides, coated or otherwise, such as for example nanopigments of oxides of titanium (amorphous or crystallized in rutile and/or anatase form), of iron, of zinc, of zirconium or of cerium which are all photoprotective UV-screening agents well known per se. Conventional coating agents are moreover alumina and/or aluminum stearate. Such nanopigments of metal oxides, coated or uncoated, are in particular described in patent applications EP-A-0518772 and EP-A-0518773.

The radiation-screening agents in accordance with the invention are generally present in the compositions according to the invention in proportions ranging from 0.1% to 20% by weight relative to the total weight of the composition, and preferably ranging from 0.2% to 15% by weight relative to the total weight of the composition.

The compositions according to the invention may also contain agents for artificial tanning and/or bronzing of the skin (self-tanning agents), and more particularly dihydroxyacetone (DHA).

Another subject of the invention consists in the use of a composition according to the invention as a self-tanning product and/or for artificial bronzing of the skin.

The compositions according to the invention may in particular be intended for preventing the formation of free radicals in contact with the skin and/or for neutralizing the free radicals already formed.

The compositions according to the invention may contain, in addition, one or more anti-pollution agents and/or anti-free radical agents.

The expression "anti-pollution agent" is understood to mean any compound capable of trapping ozone, mono- or polycyclic aromatic compounds as benzopyrene and/or heavy metals such as cobalt, mercury, cadmium and/or nickel. The expression "anti-free radical agent" is understood to mean any compound capable of trapping free radicals.

As ozone scavengers which can be used in the composition according to the invention, there may be mentioned in particular phenols and polyphenols, in particular tannins, ellagic acid and tannic acid; epigallocatechin and natural extracts containing it; extracts of olive leaves; tea, in particular green tea, extracts; anthocyanins; flavonoids, in particular rutin and alpha-glycosylrutin; rosemary extracts; phenol acids, in particular chorogenic acid; stilbenes, in particular resveratrol; derivatives of sulphur amino acids, in particular S-carboxymethylcysteine; ergothioneine; N-acetylcysteine; chelators such as N,N'-bis(3,4,5-trimethoxybenzyl)ethylenediamine or one of its salts, metal complexes or esters; carotenoids such as crocetin; and various raw materials such as the mixture of arginine, histidine ribonucleate, mannitol, adenosine triphosphate, pyridoxine, phenylalanine, tyrosine and hydrolyzed RNA marketed by Laboratoires Serobiologiques under the trademark CPP LS 2633-12F®, the water-soluble fraction of maize marketed by the company SOLABIA under the trademark Phytovityl®, the mixture of fumitory extract and of lemon extract marketed under the name Unicotrozon C-49® by the company Induchem, and the mixture of extracts of ginseng, apple, peach, wheat and barley sold by the company PROVITAL under the trademark Pronalen Bioprotect®.

As scavengers of mono- or polycyclic aromatic compounds which can be used in the composition according to the invention, there may be mentioned in particular tannins such as ellagic acid; indole derivatives, in particular indole-3-carbinol; tea, in particular green tea, extracts, extracts of water hyacinth or *Eichornia crassipes*; and the water-soluble fraction of maize marketed by the company SOLABIA under the trademark Phytovityl®.

Finally, as heavy metal scavengers which may be used in the composition according to the invention, there may be mentioned, in particular, chelating agents such as EDTA, the pentasodium salt of ethylenediaminetetramethylenephosphonic acid, and N,N'-bis(3,4,5-trimethoxybenzyl) ethylenediamine or one of its salts, metal complexes or esters; phytic acid; chitosan derivatives; tea, in particular green tea, extracts; tannins such as ellagic acid; sulphur amino acids such as cysteine; extracts of water hyacinth (*Eichornia crassipes*); and the water-soluble fraction of maize marketed by the company SOLABIA under the trademark Phytovityl®.

The anti-free radical agents which can be used in the composition according to the invention comprise, in addition to certain anti-pollution agents mentioned above, vitamin E and its derivatives such as tocopheryl acetate; bioflavonoids; coenzyme Q10 or ubiquinone; certain enzymes such as catalase, superoxide dismutase, lactoperoxidase, glutathione peroxidase and quinone reductases; glutathione; benzylidenecamphor; benzylcyclanones; substituted naphthalenones; pidolates; phytantriol; gamma-oryzanol; lignans such as nordihydroguaiaretic acid (NDGA); and melatonin.

The compositions according to the invention may also be used for treating hair damaged by the harmful effects of UV radiation and of pollution. They may further contain one or more inhibitors of lysyl and/or prolyl hydroxylase.

Preferred examples of lysyl and/or propyl hydroxylase inhibitors which can be used in the composition according to the present invention are 2,4-diaminopyrimidine 3-oxide or 2,4-DPO, which is described in patent application WO 96/09048, and 2,4-diamino-6-piperidinopyrimidine 3-oxide or "Minoxidil", which is described in patents U.S. Pat. No. 4,139,619 and U.S. Pat. No. 4,596,812.

The compositions according to the invention may be used for treating skin damaged by the harmful effects of UV radiation and pollution, and in particular for treating skin dried, cracked, irritated or burnt by the sun or pollution. These compositions may further contain one or more active agents chosen from desquamating agents; moisturizing agents; anti-inflammatory agents; agents acting on the energy metabolism of the cells, or mixtures thereof.

The expression "desquamating agent" is understood to mean any compound capable of acting:

either directly on desquamation by promoting exfoliation, such as β-hydroxy acids, in particular salicylic acid and its derivatives (including 5-n-octanoylsalicylic acid); α-hydroxy acids, such as glycolic, citric, lactic, tartaric, malic or mandelic acids; urea; gentisic acid; oligofucoses; cinnamic acid; *Sophora japonica* extract; resveratrol;

or on the enzymes involved in desquamation or the degradation of corneodesmosomes, glycosidases, stratum corneum chymotryptic enzyme (SCCE), or even other proteases (trypsin, chymotrypsin-like). There may be mentioned agents which chelate inorganic salts: EDTA; N-acyl-N,N',N'-ethylenediaminetriacetic acid; aminosulphonic compounds, and in particular N-2-hydroxyethylpiperazine-N-2-ethanesulphonic acid (HEPES); 2-oxothiazolidine-4-carboxylic acid (procysteine) derivatives; methylglycinediacetic acid and its salts (TRILON M from BASF); glycine-type alpha-amino acid derivatives (as described in EP-0 852 949); honey; sugar derivatives such as O-octanoyl-6-D-maltose and N-acetylglucosamine.

The expression "moisturizing agent" is understood to mean:

either a compound acting on the barrier function, so as to keep the stratum corneum moisturized, or an occlusive compound. There may be mentioned ceramides, petroleum jelly and lanolin, sphingoid-based compounds, lecithins, glycosphingolipids, phospholipids, cholesterol and its derivatives, phytosterols (stigmasterol, β-sitosterol, campesterol), essential fatty acids, 1,2-diacylglycerol, 4-chromanone, pentacyclic triterpenes such as ursolic acid;

or a compound which directly increases the water content of the stratum corneum such as trehalose and its derivatives, hyaluronic acid and its derivatives, glycerol, pentanediol, sodium pidolate, serine, xylitol, sodium lactate, glyceryl polyacrylate, ectoin and its derivatives, chitosan, oligo- and polysaccharides, cyclic carbonates, N-lauroylpyrrolidonecarboxylic acid and N-α-benzoyl-L-arginine;

or a compound activating the sebaceous glands, such as steroid derivatives (including DHEA) and vitamin D and its derivatives.

The expression "anti-inflammatory agent" is understood to mean any compound capable of inhibiting the principal enzymes involved in the inflammatory process (arachidonic acid cascade), namely: phospholipases A2 (PLA2); lipoxygenases (Lox); and human prostaglandin synthetases (HPGS).

Among the raw materials which are effective for inhibiting at least one of these enzymes, the following active agents may be mentioned, without limitation:

pentacyclic triterpenes and plant extracts (e.g.: *Glycyrrhiza glabra*) containing them, such as β-glycyrrhetinic acid and its salts and/or its derivatives (glycyrrhetic acid monoglucuronide, stearyl glycyrrhetinate, 3-stearoyloxyglycyrrhetic acid), ursolic acid and its salts, oleanolic acid and its salts, betulinic acid and its salts, *Paeonia suffruticosa* and/or *lactiflora* extracts, calophyllum oil, salicylic acid salts and in particular zinc salicylate, anti-inflammatory phycosaccharides (hydrolyzed algin or hydrolyzed algin and zinc sulphate) from the company Codif, phlorogine (*Laminaria saccharina*) from Secma, canola oil, tamanu oil, calophyllum oil, α-bisabolol and camomile extracts, allantoin, omega-3 unsaturated oils such as rose musk oil, blackcurrant seed oil, echium oil, fish oil, omega plankton (plankton extract) from Secma, lipacide C8G (capriloylglycine) from Seppic, Seppicalm VG (sodium palmitoylproline and nymphea alba) from Seppic, extract of rosebay willow-herb, extract of pygeum, Soothex (extract of *Boswellia serrata*) from Quest, phytoplenolin (*Centipeda cunnighami* extract) from Bio-Botanica, helioxine (*Helianthus annuus* extract) from Silab, Sensiline (*Linum usitatissimum*) from Silab, tocotrienols, Cola nitida extracts, piperonal, clove extract, extract of rosebay willow-herb (*Epilobium angustifolium*), Aloe vera, bacocalmine (*Bacopa moniera* extract) from Séderma, phytosterols, cortisone, hydrocortisone, indomethacin and betamethasone.

The active agents which act on energy metabolism in the cells are those which act on the skin energy metabolism such as, for example, and without limitation, ATP synthesis, those involved in the respiratory chain in the cell and on energy reserves. There may be mentioned Coenzyme Q10 (ubiquinone), cytochrome C, creatine or phosphocreatine.

The compositions according to the invention may be used to prevent and/or treat the signs of skin aging, in particular of photoaging of the skin, and in particular the loss of firmness and/or elasticity of the skin.

They may further contain one or more active agents chosen from the group consisting of antiglycation agents; NO-synthase inhibitors; agents which stimulate the synthesis of dermal or epidermal macromolecules and/or which prevent their degradation; agents which stimulate proliferation of the fibroblasts; muscle relaxants; tightening agents.

The expression "antiglycation agent" is understood to mean a compound which prevents and/or reduces the glycation of the skin proteins, in particular of the proteins of the dermis, such as collagen.

Examples of antiglycation agents are plant extracts of the Ericaceae family, such as an extract of bilberry (*Vaccinium angusfifollium*); ergothioneine and its derivatives; and hydroxystilbenes and their derivatives, such as resveratrol and 3,3',5,5'-tetrahydroxystilbene. These antiglycation agents are described in applications FR 99/16166, FR 00/08158, FR 99/09267 and FR 99/16168, respectively. Resveratrol is particularly preferred for use in this invention.

Examples of NO-synthase inhibitors suitable for use in the present invention comprise in particular a plant extract of the species *Vitis vinifera* which is in particular marketed by the company Euromed under the name "Leucocyanidines de raisins extra", or by the company Indena under the name Leucoselect®, or finally by the company Hansen under the name "Extrait de marc de raisin"; a plant extract of the species *Olea europaea* which is preferably obtained from olive leaves and is marketed in particular by the company VINYALS as a dry extract, or by the company Biologia & Technologia under the trademark Eurol BT; and an extract of a plant of the species Gingko biloba which is preferably a dry aqueous extract of this plant sold by the company Beaufour under the trademark "Gingko biloba extrait standard".

Among the active agents stimulating the macromolecules of the dermis, there may be mentioned those which act:

either on the synthesis of collagen, such as *Centella asiatica* extracts; asiaticosides and derivatives; synthetic peptides such as lamin, biopeptide CL or palmitoyloligopeptide marketed by the company SEDERMA; peptides extracted from plants, such as the soya bean hydrolyzate marketed by the company COLETICA under the trademark Phytokine®; and plant hormones such as auxins;

or on the synthesis of elastin, such as the *Saccharomyces cerevisiae* extract marketed by the company LSN under the trademark Cytovitin®; and the extract of the alga *Macrocystis pyrifera* marketed by the company SECMA under the trademark Kelpadelie®;

or on the synthesis of glycosaminoglycans, such as the product of the fermentation of milk by *Lactobacillus vulgaris*, marketed by the company BROOKS under the trademark Biomin yogourth®; the extract of a brown alga *Padina pavonica* marketed by the company ALBAN MÜLLER under the trademark HSP3®; and the *Saccharomyces cerevisiae* extract which is available in particular from the company SILAB under the trademark Firmalift® or from the company LSN under the trademark Cytovitin®;

or on the synthesis of fibronectin, such as the extract of a zooplankton Salina marketed by the company SEPORGA under the trademark GP4G®; the yeast extract available in particular from the company ALBAN MÜLLER under the trademark Drieline®; and the palmitoyl pentapeptide marketed by the company SEDERMA under the trademark Matrixil®;

or on the inhibition of metalloproteinases (MMP) such as more particularly MMP 1, 2, 3 and 9. There may be mentioned: retinoids and derivatives, isoflavonoids, oligopeptides and lipopeptides, lipoamino acids, malt extract marketed by the company COLETICA under the trademark Collalift®; bilberry or rosemary extracts; lycopene; isoflavones, their derivatives or plant extracts containing them, in particular the extracts of soya bean (marketed for example by the company ICHIMARU PHARCOS under the trademark Flavosterone SB®), of red clover, of flax, of kakkon or of sage;

or on the inhibition of serine proteases, such as leukocyte elastase or cathepsin G. There may be mentioned: the peptide extract of seeds of leguminous plants (*Pisum sativum*) which is marketed by the company LSN under the trademark Parelastyl®; heparinoids; and pseudo-dipeptides.

Among the active agents stimulating epidermal macromolecules such as fillagrin and keratins, there may be mentioned in particular the lupin extract marketed by the company SILAB under the trademark Structurin®; the extract of buds of a beech *Fagus sylvatica* marketed by the company GATTEFOSSE under the trademark Gatuline®; and the extract of a zooplankton Salina marketed by the company SEPORGA under the trademark GP4G®.

The agents stimulating the proliferation of fibroblasts which can be used in the composition according to the invention may, for example, be chosen from plant proteins or polypeptides, extracts, in particular from soya bean (for example a soya bean extract marketed by the company LSN under the name Eleseryl SH-VEG 8® or marketed by the company SILAB under the trademark Raffermine®); and plant hormones such as gibberellins and cytokinins.

The agents stimulating the proliferation of keratinocytes, which can be used in the composition according to the invention, comprise in particular retinoids such as retinol and its esters, including retinyl palmitate; extracts of nut oil cakes marketed by the company GATTEFOSSE; and *Solanum tuberosum* extracts marketed by the company SEDERMA.

The agents stimulating the differentiation of keratinocytes comprise, for example, minerals such as calcium; the lupin extract marketed by the company SILAB under the trademark Photopreventine®; sodium beta-sitosterylsulphate marketed by the company SEPORGA under the trademark Phytocohesine®; and the maize extract marketed by the company SOLABIA under the trademark Phytovityl®.

The muscle relaxants which can be used in the composition according to the invention comprise calcium inhibitors such as alverine and its salts, chloride channel openers such as Diazepam, and inhibitors of catecholamines and of acetylcholine such as the hexapeptide argireline® marketed by the company LIPOTEC.

Among the tightening agents which can be used in the composition according to the present invention, there may be mentioned in particular:

(1) polyurethane latexes or acrylic-silicone latexes, in particular those described in patent application EP-1038519, such as a polydimethylsiloxane grafted with propylthio (polymethyl acrylate), propylthio(polymethyl methacrylate) and propylthio(polymethacrylic acid), or alternatively a polydimethylsiloxane grafted with propylthio(polyisobutyl methacrylate) and propylthio (polymethacrylic acid). Such graft silicone polymers are in particular sold by the company 3M under the trademarks VS 80, VS 70 or LO21, (2) vegetable proteins from soya bean or wheat, and/or (3) sodium and magnesium silicates (laponites) and/or (4) colloidal particles of inorganic fillers, in particular of silica.

The compositions according to the invention may also be used for preventing or reducing the formation of pigmented spots and/or for lightening or depigmenting the skin. They may further contain one or more depigmenting agents and/or propigmenting agents.

The depigmenting agents which may be incorporated into the composition according to the invention comprise, for example, the following compounds: kojic acid; ellagic acid; arbutin and its derivatives such as those described in applications EP-895,779 and EP-524,109; hydroquinone; aminophenol derivatives such as those described in applications WO 99/10318 and WO 99/32077, and in particular N-cholesteryloxycarbonyl-para-aminophenol and N-ethyloxycarbonyl-para-aminophenol; iminophenol derivatives, in particular those described in application WO 99/22707; L-2-oxothiazolidine-4-carboxylic acid or procysteine, and its salts and esters; and extracts of plants, in particular of liquorice, saxifrage, guava, pear, grape, mulberry and skull cap, this list not being limiting.

As propigmenting agent, there may be mentioned the extract of burnet (*Sanguisorba officinalis*) marketed by the company MARUZEN and the extracts of chrysanthemum (*Chrysanthemum morifolium*).

The compositions in accordance with the present invention may comprise, in addition, conventional cosmetic adjuvants, chosen in particular from fatty substances, organic solvents, ionic or nonionic thickeners, demulcents, humectants, opacifiers, stabilizers, emollients, silicones, antifoaming agents, insect repellents, perfumes, preservatives, anionic, cationic, nonionic, zwitterionic or amphoteric surfactants, antagonists of substance P, antagonists of substance CGRP, fillers, polymers, propellants, alkalinizing or acidifying agents or any other ingredient customarily used in the cosmetic and/or dermatological field.

The fatty substances may consist of an oil or a wax or mixtures thereof. The expression oil is understood to mean a compound which is liquid at room temperature. The expression wax is understood to mean a compound which is solid or substantially solid at room temperature, and whose melting point is generally greater than 35° C.

As oils, there may be mentioned mineral oils (paraffin); vegetable oils (sweet almond, macadamia, blackcurrant seed or jojoba oil); synthetic oils such as perhydrosqualene, fatty alcohols, acids or esters (such as $C_{12}$–$C_{15}$ alcohol benzoate sold under the trademark "Finsolv TN" by the company WITCO, octyl palmitate, isopropyl lanolate, triglycerides, including those of capric/caprylic acids), oxyethylenated or oxypropylenated fatty esters and ethers; silicone oils (cyclomethicone, polydimethylsiloxanes or PDMS) or fluorinated oils, polyalkylenes.

As waxy compounds, there may be mentioned paraffin, carnauba wax, beeswax, hydrogenated castor oil.

Among the organic solvents, there may be mentioned lower alcohols and polyols. The latter may be chosen from glycols and glycol ethers such as ethylene glycol, propylene glycol, butylene glycol, dipropylene glycol or diethylene glycol.

The thickeners may be chosen in particular from crosslinked polyacrylic acids, polymers of acrylamidomethylpropane sulphonic acid (AMPS) such as polyacrylamide/isoparaffin/laureth-7 (Sepigel 305), stearic acid, fatty alcohols, xanthan gums, guar gums, modified or unmodified celluloses such as hydroxypropylated guar gum, methylhydroxyethylcellulose and hydroxypropylmethylcellulose.

Of course, persons skilled in the art will be careful to choose the possible additional compounds cited above and/or their quantities such that the advantageous properties intrinsically attached to the combination in accordance with the invention are not, or not substantially, altered by the addition(s) envisaged.

The compositions according to the invention may be prepared according to techniques well known to persons skilled in the art, in particular those intended for the preparation of oil-in-water or water-in-oil type emulsions.

This composition may be provided in particular in the form of a simple or complex (O/W, W/O, O/W/O or W/O/W) emulsion such as a cream, a milk, or in the form of a gel or of a gel cream, in the form of a lotion, a powder, a solid stick and may be optionally packaged as an aerosol and may be provided in the form of a mousse or a spray.

Preferably, the compositions according to the invention are provided in the form of an oil-in-water or water-in-oil emulsion.

In the case of an emulsion, the aqueous phase thereof may comprise a nonionic vesicular dispersion prepared according to known methods (Bangham, Standish and Watkins. J. Mol. Biol. 13, 238 (1965), FR-2,315,991 and FR-2,416,008).

When the cosmetic composition according to the invention is used for the care of the human epidermis, it may be provided in the form of a suspension or a dispersion in solvents or fatty substances, in the form of a nonionic vesicular dispersion or in the form of an emulsion, preferably of the oil-in-water type, such as a cream or a milk, in the form of an ointment, a gel, a gel cream, a solid stick, a powder, an aerosol mousse or a spray.

When the cosmetic composition according to the invention is used for hair care, it may be provided in the form of a shampoo, a lotion, a gel, an emulsion, a nonionic vesicular dispersion and may constitute, for example, a rinse-out composition to be applied before or after a shampoo, before or after dyeing or bleaching, before, during or after permanent waving or hair straightening, a hair styling or treatment lotion or gel, a lotion or a gel for blow drying or hair setting, a composition for permanent waving or hair straightening, for dyeing or bleaching the hair.

When the composition is used as a care product for the nails, the lips, the eyelashes, the eyebrows, it may be provided in an anhydrous or aqueous, solid or pasty form, as oil-in-water or water-in-oil emulsions, nonionic vesicular dispersions or suspensions, in the form of a solid stick.

In order to further illustrate the present invention and the advantages thereof, the following specific examples are given, it being understood that same are intended only as illustrative and in nowise limitative.

Test of Solubility:

Two amide oils in accordance with the invention are compared to 13 conventional oils used in cosmetics. Their solubilizing power is studied on a mixture of tetrahydrocurcuminoids of formula (I): i.e., the commercial product Tetrahydrocurcuminoids CG from Sabinsa as defined above.

Procedure:

1 g of a mixture of tetrahydrocurcuminoids is weighed and adjusted to 10 g with the oil studied. The mixture is heated for 15 minutes on a waterbath at 80° C. It is allowed to cool for 24 hours at room temperature and a microscopic examination is performed.

TABLE I

| OILY COMPOSITION | OIL TESTED | SOLUBILITY AFTER 24 HOURS AT ROOM TEMPERATURE |
|---|---|---|
| 1 (invention) | N-ethyl-N-butylacetylaminopropionate | no crystals |
| 2 (invention) | isopropyl N-lauroylsarcosinate | no crystals |
| 3 comparative | liquid paraffin | crystals + deposit |
| 4 comparative | dicaprylyl maleate | crystals + deposit |
| 5 comparative | $C_{12-15}$ alkyl benzoate | crystals + deposit |
| 6 comparative | liquid Jojoba wax | crystals + deposit |
| 7 comparative | refined apricot stone oil | crystals + deposit |
| 8 comparative | isohexadecane | crystals + deposit |
| 9 comparative | dicaprylyl carbonate | crystals + deposit |
| 10 comparative | triglycerides of caprylic/capric acids | crystals + deposit |
| 11 comparative | tridecyl trimellitate | crystals + deposit |
| 12 comparative | cyclopentadimethylsiloxane | crystals + deposit |
| 13 comparative | dioctyl malate | crystals + deposit |
| 14 comparative | isopropyl palmitate | crystals + deposit |
| 15 comparative | isononyl isononanoate | crystals + deposit |

Only the oils containing, in their structure, an amide unit in accordance with the invention: isopropyl N-lauroyl sarcosinate and N-ethyl-N-butylaminopropionate, make it possible to completely dissolve the mixture of tetrahydrocurcuminoids.

Stability as a Formulation:

The mixture of tetrahydrocurcuminoids of the formula (I) (Tetrahydrocurcuminoids CG from Sabinsa) was formulated at 0.5% in three O/W emulsions by varying the nature of the solvent used to solubilize the said mixture. The compositions of the formulas tested are described below and the quantities are expressed in grams.

TABLE II

| COMPOSITIONS TESTED | A (Not In Accordance With The Invention) | B (Invention) | C (Invention) |
|---|---|---|---|
| Mixture of cetylstearyl alcohol and of oxyethylenated (33 EO) cetylstearyl alcohol 80/20 | 7 | 7 | 7 |
| Mixture of glyceryl mono- and distearate | 2 | 2 | 2 |
| Cetyl alcohol | 1.5 | 1.5 | 1.5 |

TABLE II-continued

| COMPOSITIONS TESTED | A (Not In Accordance With The Invention) | B (Invention) | C (Invention) |
|---|---|---|---|
| Polydimethylsiloxane | 1 | 1 | 1 |
| Liquid paraffin | 15 | 15 | 15 |
| Butyl methoxydibenzoylmethane | 3 | 3 | 3 |
| Glycerine | 20 | 20 | 20 |
| Preservatives | 1.2 | 1.2 | 1.2 |
| Mixture of tetrahydrocurcuminoids of formula (I) (Tetrahydrocurcuminoids CG from Sabinsa) | 0.5 | 0.5 | 0.5 |
| Dioctyl malate | 7 | | |
| Isopropyl N-lauroylsarcosinate | | 7 | |
| N-Ethyl-N-butylacetylaminopropionate | | | 7 |
| Demineralized water qs | 100 g | 100 g | 100 g |

Method for Evaluating the Stability of the Formulas:

After 1 month of storage at room temperature, the stability of these formulas is microscopically evaluated, in order to detect the presence of crystals of tetrahydrocurcuminoids.

TABLE III

| COMPOSITIONS TESTED | A (Not In Accordance With The Invention) | B (Invention) | C (Invention) |
|---|---|---|---|
| Microscopic appearance | presence of numerous crystals | no crystals | no crystals |

In an emulsion, solubilizing the mixture of tetrahydrocurcuminoids in an oil having, in its structure, at least one amide unit in accordance with the invention, makes it possible to obtain good stability over time.

Each patent, patent application and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable cosmetic/dermatological composition including a cosmetically/dermatologically acceptable at least one fatty phase carrier, also comprising at least one tetrahydrocurcumin compound or derivative thereof and, as a stabilizing agent therefor, a solubilizing amount of at least one oil which contains at least one amide structural unit.

2. The cosmetic/dermatological composition as defined by claim 1, said at least one tetrahydrocurcumin compound or derivative thereof comprising a 1,7-diphenyl-3,5-heptanedione having the following structural formula (I).

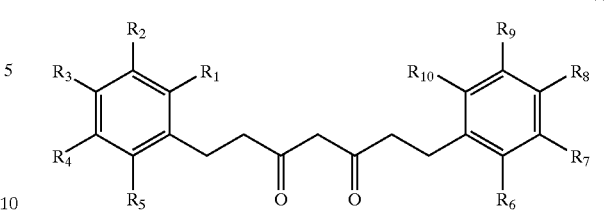

in which the radicals $R_1$, $R_2$, $R_3$, $R_4$, $R_5$, $R_6$, $R_7$, $R_8$, $R_9$ and $R_{10}$, which may identical or different, are each (i) a hydrogen atom; (ii) a linear or branched $C_1-C_4$ alkyl radical; (iii) a radical $OR_{11}$ in which $R_{11}$ is a hydrogen atom, a linear or branched $C_1-C_4$ alkyl radical, a radical $PO(OX_1)(OX_2)$ or a radical $SO_2(OX_3)$ in which $X_1$, $X_2$ and $X_3$, which may be identical or different, are each a hydrogen atom or an alkali metal cation or $NH_4^+$, with the proviso that $X_1$ and $X_2$ may together be a divalent metal cation; (iv) an acyl radical $R_{12}CO$ in which $R_{12}$ is a $C_1-C_{30}$ hydrocarbon radical, which may be linear or branched, saturated or unsaturated, hydroxylated or nonhydroxylated, carboxylated or noncarboxylated; (v) a glycosyl or uronyl radical; with the proviso that, when a radical $R_1$ to $R_{10}$ is a radical $OR_{11}$, it can also form with the a aromatic ring to which it is bonded and an adjacent radical a ring member containing 5 or 6 atoms; with the proviso that the radicals $OR_3$ and $OR_8$ may together form with the aromatic ring to which they are bonded and the radicals $R_2$ or $R_4$ and $R_7$ or $R_9$ a ring member containing 5 or 6 atoms; and with the further proviso that at least one of the radicals $R_1$ to $R_{10}$ is a radical $OR_{11}$.

3. The cosmetic/dermatological composition as defined by claim 2, said at least one compound of formula (I) being selected from the group consisting of:

(a) 1,7-bis(3-methoxy-4-hydroxyphenyl)-3,5-heptanedione or tetrahydrocurcumin (THC) having the structure:

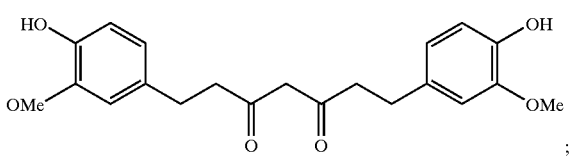

(b) 1-(3-methoxy-4-hydroxyphenyl)-7-(4'-hydroxyphenyl)-3,5-heptanedione or tetrahydrodemethoxycurcumin (THDC) having the structure:

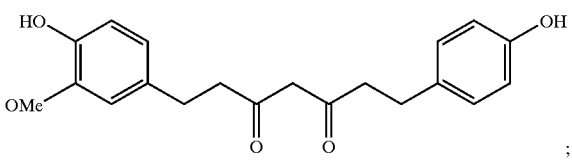

(c) 1,7-bis(4-hydroxyphenyl)-3,5-heptanedione or tetrahydrobisdemethoxycurcumin (THBDC) having the structure:

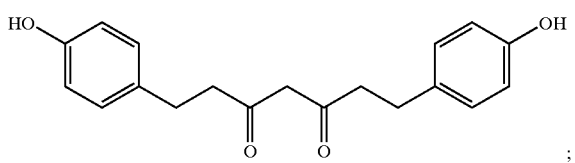

(d) 1,7-bis(3,4-dihydroxyphenyl)-3,5-heptanedione having the structure:

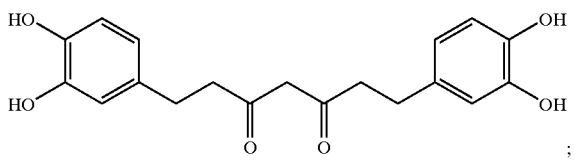

and (e) mixtures thereof.

4. The cosmetic/dermatological composition as defined by claim 3, said at least one compound of formula (I) solely being 1,7-bis(3-methoxy-4-hydroxyphenyl)-3,5-heptanedione or tetrahydrocurcumin (THC).

5. The cosmetic/dermatological composition as defined by claim 2, said at least one compound of formula (I) comprising a mixture of tetrahydrocurcumin, tetrahydrodemethoxycurcumin, and tetrahydrobisdemethoxycurcumin.

6. The cosmetic/dermatological composition as defined by claim 5, said at least one compound of formula (I) comprising a mixture of 70% to 95% by weight of tetrahydrocurcumin, 4% to 25% by weight of tetrahydrodemethoxycurcumin, and 0.5% to 10% by weight of tetrahydrobisdemethoxycurcumin.

7. The cosmetic/dermatological composition as defined by claim 6, said at least one compound of formula (I) comprising a mixture of 75% to 90% by weight of tetrahydrocurcumin, 8% to 20% by weight of tetrahydrodemethoxycurcumin; and 1% to 5% by weight of tetrahydrodemethoxycurcumin.

8. The cosmetic/dermatological composition as defined by claim 2, said at least one compound of formula (I) being completely dissolved in the cosmetically/dermatologically acceptable carrier therefor.

9. The cosmetic/dermatological composition as defined by claim 2, said at least one compound of formula (I) comprising from 0.001% of to 10% by weight thereof.

10. The cosmetic/dermatological composition as defined by claim 2, said at least one compound of formula (I) comprising from 0.01% to 5% by weight thereof.

11. The cosmetic/dermatological composition as defined by claim 2, said at least one compound of formula (I) comprising from 0.1% to 05% by weight thereof.

12. The cosmetic/dermatological composition as defined by claim 2, said at least one oil containing at least one amide structural unit having the following formula (II):

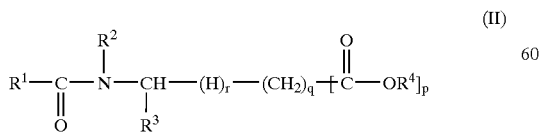

in which the radical $R^1$ represents an optionally functionalized, aliphatic, cycloaliphatic or cyclic, saturated or unsaturated, monovalent hydrocarbon radical having from 1 to 30 carbon atoms; the radicals $R^2$, $R^3$ and $R^4$, which may be identical or different, are each hydrogen or an optionally functionalized, aliphatic, cycloaliphatic or cyclic, saturated or unsaturated, monovalent hydrocarbon radical having from 1 to 30 carbon atoms; r is 0 or 1; q is an integer ranging from 0 to 2; p equals 0 or 1, with the proviso that when p=1, then r=0 and when p=0, then q=0 and r=0.

13. The cosmetic/dermatological composition as defined by claim 12, wherein the at least one oil of formula (II), $R^1$ is a linear or branched $C_1$–$C_{22}$ alkyl radical, a linear or branched $C_2$–$C_{22}$ alkenyl radical or an aryl radical; $R^2$ is a hydrogen atom or a linear or branched $C_1$–$C_6$ alkyl radical; $R^3$ is a hydrogen atom or a linear or branched $C_1$–$C_6$ alkyl radical; and $R^4$ is a linear or branched $C_1$–$C_{10}$ alkyl radical, a linear or branched $C_2$–$C_{10}$ alkenyl radical or a sterol residue.

14. The cosmetic/dermatological composition as defined by claim 13, wherein the at least one oil of formula (II) the radical $R^1$ (CO)— is an acyl group of an acid selected from the group consisting of acetic acid, toluic acid, capric acid, lauric acid, myristic acid, palmitic acid, stearic acid behenic acid, linoleic acid, linolenic acid, oleic acid, isostearic acid, 2-ethylhexanoic acid, a coconut oil fatty acid, a palm kernel oil fatty acid, and hydroxy-substituted derivatives thereof.

15. The cosmetic/dermatological composition as defined by claim 13, wherein the at least one oil of formula (II), p equals 1 and the moiety —N($R^2$)CH($R^3$) (CH2)q(CO)— of the amino acid ester is selected from those of the amino acids glycine, alanine, valine, leucine, isoleucine, serine, threonine, proline, hydroxyproline, β-alanine, N-butyl-β-alanine, aminobutyric acid, aminocaproic acid, sarcosine or N-methyl-β-alanine.

16. The cosmetic/dermatological composition as defined by claim 13, wherein the at least one oil of formula (II), p equals 1 and the moiety of the amino acid esters corresponding to the group $OR^4$ is obtained from alcohol is selected from the group consisting of methanol, ethanol, propanol, isopropanol, butanol, tert-butanol, isobutanol, 3-methyl-1-butanol, 2-methyl-1-butanol, pentanol, hexanol, cyclohexanol, octanol, 2-ethylhexanol, decanol, lauryl alcohol, myristyl alchol, cetyl alcohol, ketostearyl alcohol, stearyl alcohol, oleyl alcohol, behenyl alcohol, jojoba alcohol, 2-hexadecyl alcohol, 2-octyldodecanol alcohol and isostearyl alcohol.

17. The cosmetic/dermatological composition as defined by claim 13, said at least one oil of formula (II) being selected from the group consisting of:

N-acetyl-N-butylaminopropionate having the following formula:

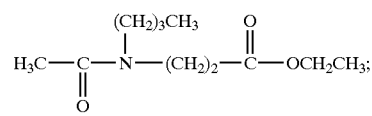

isopropyl N-lauroylsarcosinate having the following formula:

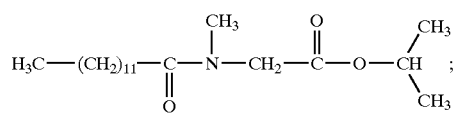

N,N-diethyltoluamide having the following formula:

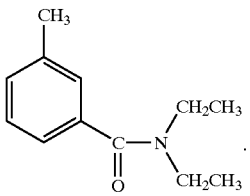

18. The cosmetic/dermatological composition as defined by claim 12, said at least one oil of formula (II) comprising from 0.1% to 40% by weight thereof.

19. The cosmetic/dermatological composition as defined by claim 12, said at least one oil of formula (II) comprising from 1% to 20% by weight thereof.

20. The cosmetic/dermatological composition as defined by claim 12, said at least one oil containing at least one amide structural unit being present in such quantity as to solubilize the total quantity of said at least one compound.

21. The cosmetic/dermatological composition as defined by claim 1, further comprising at least one UV radiation-screening agent.

22. The cosmetic/dermatological composition as defined by claim 21, said at least one ultraviolet radiation-screening agent comprising an organic UV screening agent, an inorganic UV screening agent or mixture thereof.

23. The cosmetic/dermatological composition as defined by claim 22, comprising at least one organic UV screening agent selected from the group consisting of anthranilates; cinnamic derivatives; dibenzoylmethane derivatives; salicylic derivatives; camphor derivatives; triazine derivatives; benzophenone derivatives; β,β'diphenylacrylate derivatives, benzotriazole derivatives; benzimidazole derivatives; imidazolines; bis-benzoazolyl derivatives; p-aminobenzoic acid derivatives (PABA); methylene bis(hydroxyphenylbenzotriazole) derivatives; screening polymers and screening silicones; dimers derived from α-alkylstyrene; 4,4-diarylbutadiene derivatites; amino-substituted hydroxybenzophenones; and mixtures thereof.

24. The cosmetic/dermatological composition as defined by claim 23, said at least one organic UV screening agent being selected from the group consisting of:

Ethylhexyl Salicylate,
Butyl Methoxydibenzoylmethane,
Ethylhexyl Methoxycinnamate,
Octocrylene,
Phenylbenzimidazole Sulfonic Acid,
Terephthaiylidene Dicamphor Sulfonic Acid,
Benzophenone-3,
Benzophenone-4,
Benzophenone-5,
n-Hexyl 2-(4-diethylamino-2-hydroxybenzoyl)benzoate,
4-Methylbenzylidenecamphor,
Disodium Phenyl Dibenzimidazole Tetrasulfonate,
Anisotriazine,
Ethyihexyl Triazone,
Diethyihexyl Butamido Triazone,
Methylene bis-Benzotriazolyl Tetramethylbutyiphenol,
Drometrizole Trisiloxane,
Polysilicone-15,
1,1-Dicarboxy-(2,2'-dimethyl)-4,4-diphenylbutadiene, and mixtures thereof.

25. The cosmetic/dermatological composition as defined by claim 22, comprising at least one inorganic screening agent selected from the group consisting of pigments or nanopigments of metal oxides which are coated or uncoated.

26. The cosmetic/dermatological composition as defined by claim 25, said at least one inorganic screening agent comprising nanopigments of titanium, iron, zinc, zirconium or cerium oxide.

27. The cosmetic/dermatological composition as defined by claim 22, said at least one radiation screening agent comprising from 0.1% to 20% by weight thereof.

28. The cosmetic/dermatological composition as defined by claim 1, further comprising at least one self-tanning agent.

29. The cosmetic/dermatological composition as defined by claim 1, further comprising at least one anti-pollution agent and/or anti-free radical agent.

30. The cosmetic/dermatological composition as defined by claim 1, further comprising at least one lysyl and/or prolyl hydroxylase inhibitors.

31. The cosmetic/dermatological composition as defined by claim 1, further comprising at least one desquamating agent; moisturizing agent; anti-inflammatory agent; agent which acts on the energy metabolism of cells; or mixtures thereof.

32. The cosmetic/dermatological composition as defined by claim 1, further comprising at least one depigmenting agent and/or propigmenting agent.

33. The cosmetic/dermatological composition as defined by claim 1, further comprising at least one fatty substance, organic solvent, ionic or nonionic thickener, demulcent, humectant, opacifier, stabilizer, emollient, silicone, anti-foaming agent, insect repellent, perfume, preservative, anionic, cationic, nonionic, zwitterionic or amphoteric surfactant, antagonists of substance P, anti-free radical agent, antagonist of substance CGRP, filler, polymer, propellant, alkalinizing or acidifying agent or any other conventional cosmetic/dermatological additive or adjuvant.

34. A regime or regimen for preventing or combating the harmful effects of UV radiation and/or of pollution on human keratinous substrates, comprising topically applying thereon a thus effective amount of a cosmetic/dermatological composition as defined by claim 21.

35. A regime or regimen for the self-tanning and/or artificial bronzing of human skin, comprising topically applying thereon a thus effective amount of a cosmetic/dermatological composition as defined by claim 28.

36. A regime or regimen for preventing the formulation of free radicals in contact with human skin and/or neutralizing free radicals already formed thereon, comprising topically applying thereon a thus effective amount of a cosmetic/dermatological composition as defined by claim 29.

37. A regime or regimen for treating hair damaged by UV radiation and/or pollution, comprising topically applying thereon a thus effective amount of a cosmetic/dermatological composition as defined by claim 21.

38. A regime or regimen for treating human skin dried, cracked, irritated or burned by the sun and/or pollution, comprising topically applying thereon a thus effective amount of a cosmetic/dermatological composition as defined by claim 1.

39. A regime or regimen for preventing human skin aging or photoaging, comprising topically applying thereon a thus effective amount of a cosmetic/dermatological composition as defined by claim 1.

40. A regime or regimen for treating the signs of human skin aging or photoaging, comprising topically applying thereon a thus effective amount of a cosmetic/dermatological composition as defined by claim 1.

41. A regime or regimen for preventing and/or treating the loss of firmness and/or of the elasticity of human skin, comprising topically applying thereon a thus effective amount of a cosmetic/dermatological composition as defined by claim 1.

42. A regime or regimen for preventing and/or reducing the formation of pigmented spots and/or for lightening or depigmenting human skin, comprising topically applying thereon a thus effective amount of a cosmetic/dermatological composition as defined by claim 32.

43. A method for solubilizing at least one tetrahydrocurcumin compound or derivative thereof, comprising dissolving same in a thus effective amount of at least one oil which contains at least one amide structural unit.

44. The cosmetic/dermatological composition as defined by claim 1, formulated as an emulsion.

45. The cosmetic/dermatological composition as defined by claim 1, formulated as an oily gel or paste.

\* \* \* \* \*